US006281018B1

United States Patent
Kirouac et al.

(10) Patent No.: US 6,281,018 B1
(45) Date of Patent: Aug. 28, 2001

(54) SELECTIVE PURIFICATION AND ENRICHMENT SORTING OF FLOW CYTOMETER DROPLETS BASED UPON ANALYSIS OF DROPLET PRECURSOR REGIONS

(75) Inventors: William E. Kirouac, Pembroke Pines; Eric Statler, Davie; J. David Starling, Coral Gables, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/031,484

(22) Filed: Feb. 26, 1998

(51) Int. Cl.[7] .................................................. G01N 33/48
(52) U.S. Cl. ................... 436/63; 436/164; 356/73
(58) Field of Search ................... 436/63, 10, 164, 436/172; 209/571, 576; 356/72, 73

(56) References Cited

U.S. PATENT DOCUMENTS

| 3,675,768 | 7/1972 | Legorreta-Sanchez . | |
|---|---|---|---|
| 3,826,364 | 7/1974 | Bonner et al. . | |
| 4,097,373 | * | 6/1978 | Allred ..................................... 356/39 |
| 4,148,718 | * | 4/1979 | Fulwyler ............................... 209/3.1 |
| 4,447,883 | 5/1984 | Farrell et al. . | |
| 4,499,052 | * | 2/1985 | Fulwyler ............................... 422/52 |
| 4,538,733 | * | 9/1985 | Hoffman ............................... 209/3.1 |
| 4,667,830 | 5/1987 | Nozaki, Jr. et al. . | |
| 4,691,829 | * | 9/1987 | Auer ....................................... 209/3.1 |
| 4,778,593 | 10/1988 | Yamashita et al. . | |
| 4,981,580 | 1/1991 | Auer ....................................... 209/3.1 |

\* cited by examiner

Primary Examiner—Jeffrey Snay
(74) Attorney, Agent, or Firm—Charles E. Wands; Mitchell E. Alter

(57) ABSTRACT

A flow cytometer sorting mechanism is operative to controllably sort successively generated fluid droplets in accordance with the contents of a plurality of contiguous precursor regions of the carrier fluid which are contained within a target droplet of interest and precursor regions for droplets on either side of the target droplet. This multi-region sorting window scheme is particularly useful in reducing the time required to harvest a highly purified quantity of a particular type of cell, as not only are droplets containing only desired cells sorted to a highly purified collection store, but should an undesired cell be detected within a predefined proximity of a desired cell, rather than being simply aborted, the droplet is sorted into an auxiliary enrichment container, whose contents may then be reclaimed for resorting. Since all droplets are sorted to one of a plurality of droplet reclamation containers, substantially no detected/target cells are lost. As a result, through dual collection and resorting of the contents of the enrichment container the total harvest time can be significantly reduced.

37 Claims, 5 Drawing Sheets

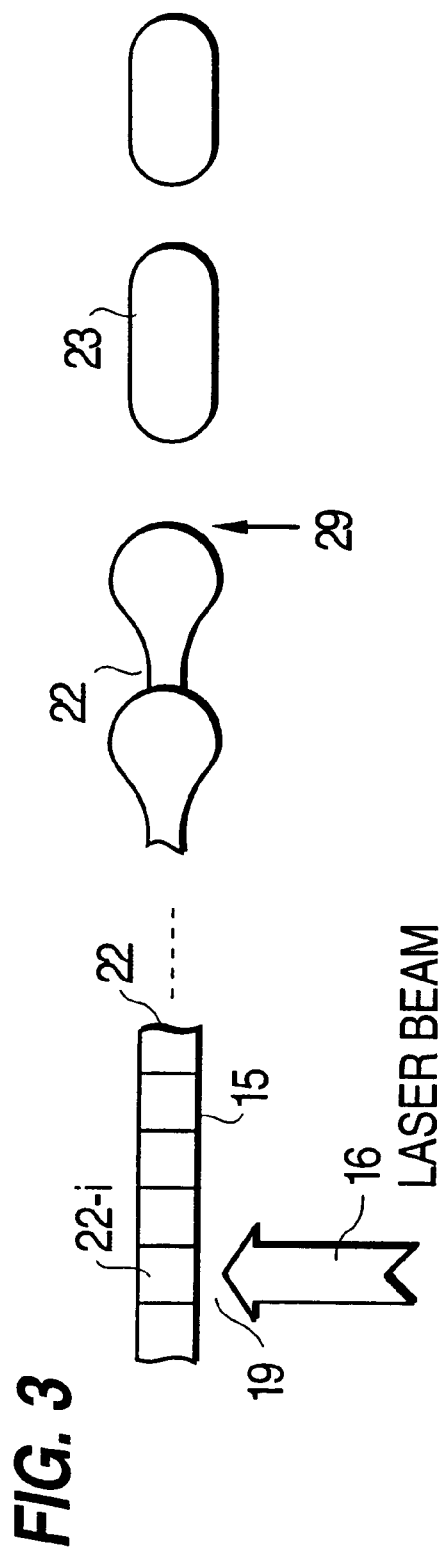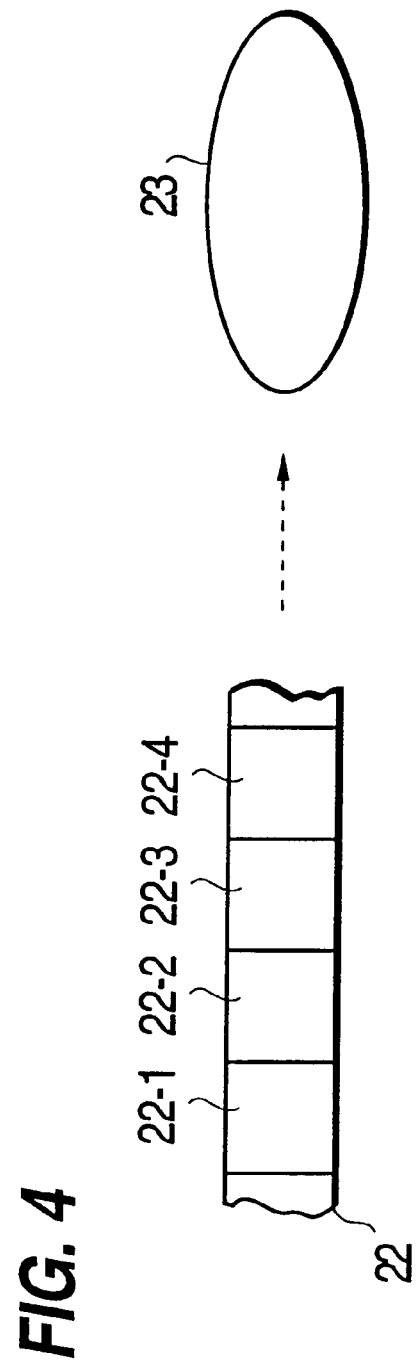
FIG. 3
FIG. 4

SELECTIVE PURIFICATION AND ENRICHMENT SORTING OF FLOW CYTOMETER DROPLETS BASED UPON ANALYSIS OF DROPLET PRECURSOR REGIONS

FIELD OF THE INVENTION

The present invention relates in general to fluid analysis systems, such as flow cytometers, and is particularly directed to a process for analyzing a fluid, such as one containing human blood cells, for the presence of prescribed constituents, such as preselected types of blood cells, and then sorting successively generated fluid droplets to a selected one of a plurality of collection stores based upon the constituency of a selected plurality of contiguous droplet precursor regions.

BACKGROUND OF THE INVENTION

Flow cytometers are commonly employed in the medical industry to analyze particles in a patient's body fluid (e.g., blood cells) as an adjunct to the diagnosis and treatment of disease. As a non-limiting example, in the course of chemotherapy treatment, such instruments may be used to sort and collect healthy blood cells (stencils) from a quantity of blood that has been removed from a patient's bone marrow prior to chemotherapy. Once a chemotherapy treatment session is completed, a collected quantity of these cells is then reinjected back into the patient, to facilitate migration and healthy blood cell reproduction.

For this purpose, as diagrammatically illustrated in FIG. 1, particles 10 to be analyzed, such as cells of a centrifuged blood sample stored in a container 12, are analyzed by injecting the particles into a (pressurized) continuous or uninterrupted carrier fluid (e.g., saline) 14, and directing the carrier fluid along a channel 15 that passes through the output beam 16 emitted by an optical illumination subsystem, such as one or more lasers 18. Located optically in the path of the laser output beam 16 after its being intercepted by the carrier fluid passing therethrough are one or more photodetectors of a photodetector subsystem 21.

This photodetector subsystem 71 is positioned to receive light as modulated by the contents of (particles/cells within) the fluid in the channel 15, including that reflected off a cell, the blocking of light by a cell, and a light emission from a fluorescent dye antibody attached to a cell. In order to avoid confusion as to which photodetector output signal is representative of which illuminated cell, the fluid flow channel through the cytometer is configured and sized to pass the particles or cells only one cell at the time through an intersection location 19 with the laser's output beam 16. As a consequence, as the output signals from the photodetector of interest is irradiated by the laser beam to the time when a droplet containing the cell of interest eventually separates from the carrier fluid stream.

The individual droplets 23 produced by the droplet generator 25 do not form immediately at the droplet generator's exit port 27, but rather break off naturally and in random fashion at location 29 downstream of the exit port 27. The point in space 29 downstream of the exit port 27 at which the droplets individually form may be adjusted by varying the parameters of the drive signal to the piezoelectric transducer of the droplet generator 25, and may be defined so as to cause the droplets 23 to become synchronized with the frequency of the piezo vibration of the droplet generator 25. As a non-limiting example, the acoustic drive frequency applied to the droplet generator 25 may be on the order for from four to one hundred Khz, at a fluid pressure on the order of from three to seventy psi.

Once the droplets 23 have been individually formed in a spaced apart sequence, they may be controllably sorted by means of droplet sorter 30 into a collection container 41, or allowed to pass unsorted along a main travel path 24 into an aborted or discarded waste container 43. The droplet sorter's electrostatic charging collar 31 may comprise a metallic ring surrounding that point in the droplet stream 22 where the individual droplets 23 separate from the fluid stream, and is typically several droplets in length. It is positioned vertically downstream of the exit port 27 of the droplet generator 25, and upstream of an subsystem 21 are modulated by the particles in the carrier fluid, each modulation signal can be associated with a respective cell in the fluid carrier stream.

If the output of the photodetector subsystem 21 satisfies prescribed 'sort' criteria associated with one or more parameters of a desired cell, then subsequent to a 'sort delay', the photodetector output signal may be used to control the sorting of a droplet of the carrier fluid containing that cell (by means of a downstream droplet sorter 30), once that droplet is formed by into a stream of droplets 23 by means of an acoustically (e.g., piezoelectric) driven droplet generator 25. For this purpose, the photodetector output is typically digitized and then analyzed by a cell type mapping or identification algorithm executed by an associated supervisory control processor. Based upon this analysis, the control processor instructs the droplet sorter to sort or abort the droplet.

The sort delay is the period of time that elapses between the instant in time at which the photodetector generates an output signal for that cell as it is illuminated by the laser beam at intersection location 19 and the time at which that portion of the fluid stream containing that cell breaks off into a droplet at some downstream location 29. The sort delay may be defined means of by a delay timer, such as a counter driven by a high speed sort control clock, so that the output of the counter indicates the time difference between the time that the portion of region of the carrier fluid containing the cell associated set of electrostatic (opposite polarity, high voltage) deflection plates 33 and 35 between which the stream of charged droplets 23 pass as they travel downwardly towards the collection and waste containers.

Under the control of a cell analysis and sorting routine executed by the system workstation 50, a prescribed charging voltage is selectively applied via deflection control circuitry 52 to the charging collar 31 at a time determined by the sort delay, thereby charging that segment of the cell-containing fluid stream, so that any droplet breaking off from the stream at that point and containing the cell of interest will carry the charge induced by the collar. Then, as an individual charged droplet carrying this charge (one of which is shown at 23C) passes between the two opposite polarity high voltage deflection plates 33 and 35, it is attracted to the plate with the opposite charge, while being simultaneously repelled by the plate with the same or like charge. For a droplet containing a cell to be sorted, this electrostatic steering action directs the charged droplet 23C along a path 26 to one side of the travel path 24 of the main stream, and into the collection container 41 placed on the side of the path of the main stream of droplets.

The location of the point 29 where an individual droplet 23 forms or breaks off from the continuous fluid stream 22 is critical to accurate sorting of the droplets, since only a droplet that breaks off from the stream at the time of the applied sort charge will be deflected by the deflection plates, and subsequently collected in the target sorting container. As described above, for any given cell 10 within the fluid stream 22, there is a 'sort' delay between the time at which the photodetector subsystem 21 generates an output signal for that cell and the time at which a droplet 23 containing that cell breaks off from the fluid stream. As described previously, during this sort delay, the output signal from the photodetector is digitized and then analyzed-processed by a droplet sort routine executed by the system's control processor (controlled by or installed within workstation 50) to determine whether the droplet containing the cell of interest is to be sorted into the collection container 41 or aborted into the waste container 43.

Since sort delay is affected, inter alia, by the pressure of the carrier fluid, size and surface characteristics of the droplet generator exit port, the viscosity of the carrier fluid, and the amplitude of the piezo vibration, a preliminary calibration cycle is conducted to accurately locate the droplet formation point. As a non-limiting example, this may be accomplished by manually placing the droplet formation point 29 at a predetermined distance from the laser intersection point 19, using a microscope objective, or a video system, to observe the fluid steam 22. By strobing a light emitting diode in sync with the excitation frequency of the drive signal to the droplet generator 25, the droplets 23 formed from the fluid stream 22 will appear to be stationary. By increasing or decreasing the amplitude of the drive signal to a piezoelectric actuator 28, the droplet formation point 29 can be moved closer or farther away from the laser intersection point 19. The system operator can then adjust the point at which the droplets first form to a reference or positioning mark.

Next, the operator inputs to the sorting system a sort delay time that has been determined on the basis of previous experimentation, so as to place the system within several droplets of the actual sort delay time. In order to bring the system to within one droplet of accuracy, the operator sets up and runs a calibration sort operation, using test beads, which mimic biological cells in terms of size. The beads are sorted onto a slide, and the slide is observed with a microscope in order to determine if the number of beads on the slide coincides with the number of beads the system reported as having sorted. If the numbers do not coincide, then the system is adjusted by changing the sort delay time, or by moving the droplet formation point by adjusting the acoustic drive signal. This operation is iteratively repeated as necessary until the beads counts are correct. With the system thus initially calibrated, it may then be monitored visually for drift, with the operator observing the fluid stream and droplets for movement. To verify that the sort parameters remain the same, the slide and bead analysis sequence described above may be repeated.

Because the particle (e.g., blood cell) processing rate of a flow cytometer is often limited to a relatively slow data rate (e.g., a range on the order of from ten to thirty thousand cells per second), then for commonplace yield rates of desired cells on the order of only five percent or less, the time required to collect or harvest a highly purified quantity of cells (e.g., on the order of a million or more), may be as long as six hours. One of the reasons for this relatively lengthy harvesting time is the fact that the sorting routine executed by the system's supervisory computer will customarily cause droplets that have been determined to contain (have in close proximity) 'events' other than only good cells to be aborted (discarded) into the waste container, even though such droplets may also contain desired cells. Once such aborted droplets containing good cells are discarded they cannot be reclaimed.

Unfortunately harvesting time cannot be reduced by simply increasing the data rate (droplet processing speed) through the cytometer, since increasing the data rate effectively decreases the separation cells and droplets, and thereby places undesired components or anomalies spatially closer to the desired cells, causing more cells (up to fifty percent) to be aborted. Also, increasing the data rate can increase system jitter. Either of these conditions may place an anomaly sufficiently close to the type of cell of interest as to cause the droplet containing the desired cell to be aborted.

SUMMARY OF THE INVENTION

In accordance with the present invention, the above-discussed drawbacks of conventional flow cytometer sorting schemes are effectively remedied by a new and improved flow cytometer sorting mechanism, that is readily executable by the system's supervisory computer for controllably sorting successively generated fluid droplets to a selected one of a plurality of collection stores, the reclaimable contents of which have a useful cell density that is elevated considerably compared with that of the contents of an original storage container, such as that containing a centrifuged blood sample.

The sorting routine of the invention is operative to sort a respective 'target' fluid droplet in accordance with the contents of a plurality of contiguous precursor regions of the carrier fluid which are contained within the target droplet of interest and precursor regions for droplets on either side of the target droplet. As will be described, this multiregion sorting window scheme is particularly useful in reducing the time required to harvest a highly purified quantity of a particular type of cell. Pursuant to one aspect of the inventive process, not only are droplets containing only desired cells sorted to a highly purified collection store, but should an undesired cell be detected within a predefined proximity of a desired cell, rather than being simply aborted, the droplet is sorted into an auxiliary 'enrichment' container, whose contents may then be reclaimed for resorting. Since all droplets are sorted to one of a plurality of reclamation containers, substantially no cells are lost, as in conventional proximity based aborting decisions. As a consequence, through dual collection and resorting of the contents of the enrichment container the total harvest time can be significantly reduced.

The instrumentation architecture of a flow cytometer system employing multiple reclaimable collection stores in accordance with the present invention includes essentially the same components of the cytometer of FIG. 1, described above, but with droplets being sortable to any of a plurality of particle reclamation containers that are arranged on opposite sides of the main droplet travel path, or unsorted directly to a waste container. By reclamation container is meant a sorted droplet collection container or store, from which a quantity of extremely pure sorted droplets may be reclaimed for further use (such as reinjection back into the patient, as in the case of chemotherapy treatment, described above), or from which a quantity of less than extremely pure, but having a considerably higher density of desired particles/cells than that of the original source may be retrieved for reprocessing through the cytometer sorting mechanism of the invention.

In association with the use of a plurality of particle reclamation containers, the sort control routine executed by the system workstation is operative to sort a respective fluid droplet based upon the contents of a plurality of contiguous droplet precursor regions within that portion of the fluid stream from which the droplet of interest will be formed, and also in adjacent portions of the fluid stream from which droplets on either side of the droplet of interest will be formed.

By droplet precursor region is meant one of a plurality of sequentially contiguous regions within the particle/cell carrier fluid that will eventually be contained within a respective droplet that has broken off from the continuous fluid stream. The term 'precursor' reflects the fact that within the fluid stream at a location upstream of the droplet separation location, in particular within that portion of the carrier fluid illuminated by the laser output beam, the fluid stream may considered to be comprised of a sequence of contiguous regions that will eventually become, but are not yet formed into an actual droplet.

The resolution to which the fluid within a respective droplet may be subdivided into a plurality of such droplet precursor regions may be established in accordance with the frequency of the clock signal, by which the sort delay between the laser beam intersection location and the downstream droplet formation location is measured, such as that used to clock a sort delay counter, described above.

For a non-limiting resolution of four droplet precursor regions per droplet, that portion of the continuous fluid flow stream, that will eventually break off from the stream and become a target droplet that is sorted into one of the plurality of reclamation containers or aborted, will comprise an interior-most or middle sequence of four droplet precursor regions within an overall sequence of twelve droplet precursor regions. Of the remaining eight regions, the first four are associated with an immediately adjacent downstream droplet and the last four are associated with an immediately adjacent upstream droplet.

In accordance with the invention, respectively different sorting modes may be executed by defining sorting criteria windows to determine whether the center or second (target) droplet in the sequence of three droplets is to be sorted or aborted and, if sorted, how it is to be sorted. As non-limiting examples, the sorting modes may include the following modes.

A maximum width, non-abort (abort off) mode has a sort window that contains all of the droplet precursor regions of the target droplet and each of its immediately adjacent droplets. This sorting mode is intended to provide the highest yield of desired cells, but also allows particles other than the desired to be collected, so that the purity of the desired cells can be expected to be less than one hundred percent. In this first sorting mode, if at least one desired cell/particle of interest is detected anywhere within the sort window (containing all twelve precursor regions for the three droplets), the target droplet is sorted to a reclamation container.

A multi-sort mode may be used to selectively sort multiple types of cells to respective reclamation containers, or selectively sort the same type of cell to different reclamation containers, based upon the cell purity within the sort window.

When sorting multiple types of cells, the target droplet will be sorted to that one of the reclamation containers that has been predetermined to collect the type of cell of interest if the following conditions are satisfied. First, at least one of the different types of cells/particles of interest must be found anywhere within a prescribed multi-precursor region sort window, such as one containing all regions of the target droplet, and an immediately contiguous region of the adjacent downstream droplet, and the immediately contiguous region of the adjacent upstream droplet. Secondly, relative to that type of cell, there must be no other event, including the other type of acceptable cell, within the sort window. This latter requirement means that if the sort window contains both types of cells it will be aborted.

When sorting the same type of cell in this mode, the target droplet is never aborted. This mode is designed to sort the target droplet containing only a given type of particle to a high purity container, but otherwise sorting the target droplet to an auxiliary enrichment container, rather than aborting the target droplet. No droplets are aborted. As a consequence, if an anomaly in the sort window prevents sorting to the high purity container what would otherwise be a target droplet containing one or more desired cells, rather than being aborted and losing what could be a significant number of desired cells, the target droplet will be sorted right to the enrichment container, the contents of which may be re-centrifuged and then processed again through the cytometer system of the invention.

In order to sort the target droplet to a high purity container, two requirements must be fulfilled. First, there must be at least one prescribed type of cell/particle within the sort window (e.g., a multi region window containing regions of the target droplet and those of adjacent downstream and upstream droplets). Secondly, there must be no other type of cell or event within the sort window. Only if both of these requirements are satisfied will the target droplet be sorted to the high purity reclamation container. For all other cases, the target droplet will be sorted to the enrichment container.

The multiregion sorting window scheme is particularly useful in reducing the time required to harvest a highly purified quantity of a particular type of cell. Not only are target droplets containing only desired cells sorted to a highly purified collection store, but should an undesired cell be detected within a predefined proximity of a desired cell, rather than being aborted and therefore lost, the target droplet is sorted into the enrichment container, whose contents may then be reclaimed for resorting. As all droplets are sorted to one of a plurality of reclamation containers, no cells are lost, as in conventional proximity based aborting decisions. As a consequence, through dual collection and resorting of the contents of the enrichment container the total harvest time can be significantly reduced.

An additional abort-on mode may be used to achieve a very high purity of desired cells by the use of a relatively narrow inclusion window. This mode employs a first, relatively narrow sorting window for desired cells only, that is bounded by a second, relatively wide exclusion window, in which the presence of any particles/cells (including the desired type of particle) will cause the target droplet to be aborted. The width of the sorting window may consist of less than or all of the droplet precursor regions of the target droplet.

BRIEF DESCRIPTION OF THE DRAWINGS

FIG. 3 diagrammatically illustrates a plurality of droplet precursor regions within the carrier fluid that will eventually be contained within a respective target droplet broken off from the continuous fluid stream;

FIG. 4 shows a set of four successively contiguous droplet precursor regions.

DETAILED DESCRIPTION

Figure 1:
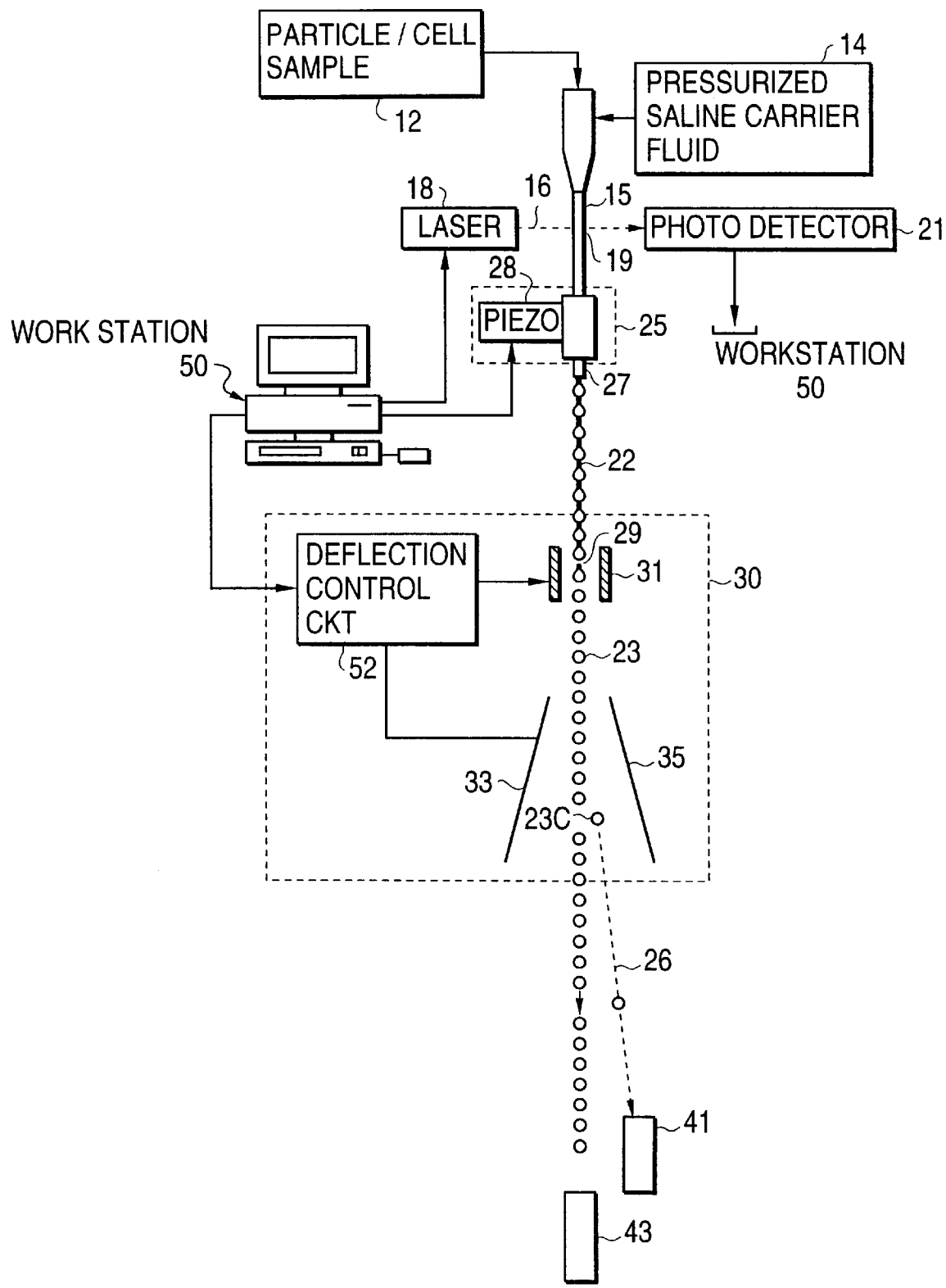
FIG. 1 diagrammatically illustrates the general instrumentation architecture of a flow cytometer.

Before describing in detail the new and improved flow cytometer sorting scheme of the present invention, it should be observed that the invention, resides primarily in what is effectively a prescribed arrangement of conventional flow cytometer instrumentation and associated digital signal processing components and attendant supervisory control circuitry therefor, that controls the operations of such circuits and components. Consequently, the configuration of such circuits components and the manner in which they are interfaced with other communication system equipment have, for the most part, been illustrated in the drawings by readily understandable block diagrams, which show only those specific details that are pertinent to the present invention, so as not to obscure the disclosure with details which will be readily apparent to those skilled in the art having the benefit of the description herein. Thus, the block diagram illustrations are primarily intended to show the major components of the flow cytometer system in a convenient functional grouping, whereby the present invention may be more readily understood.

Figure 2:
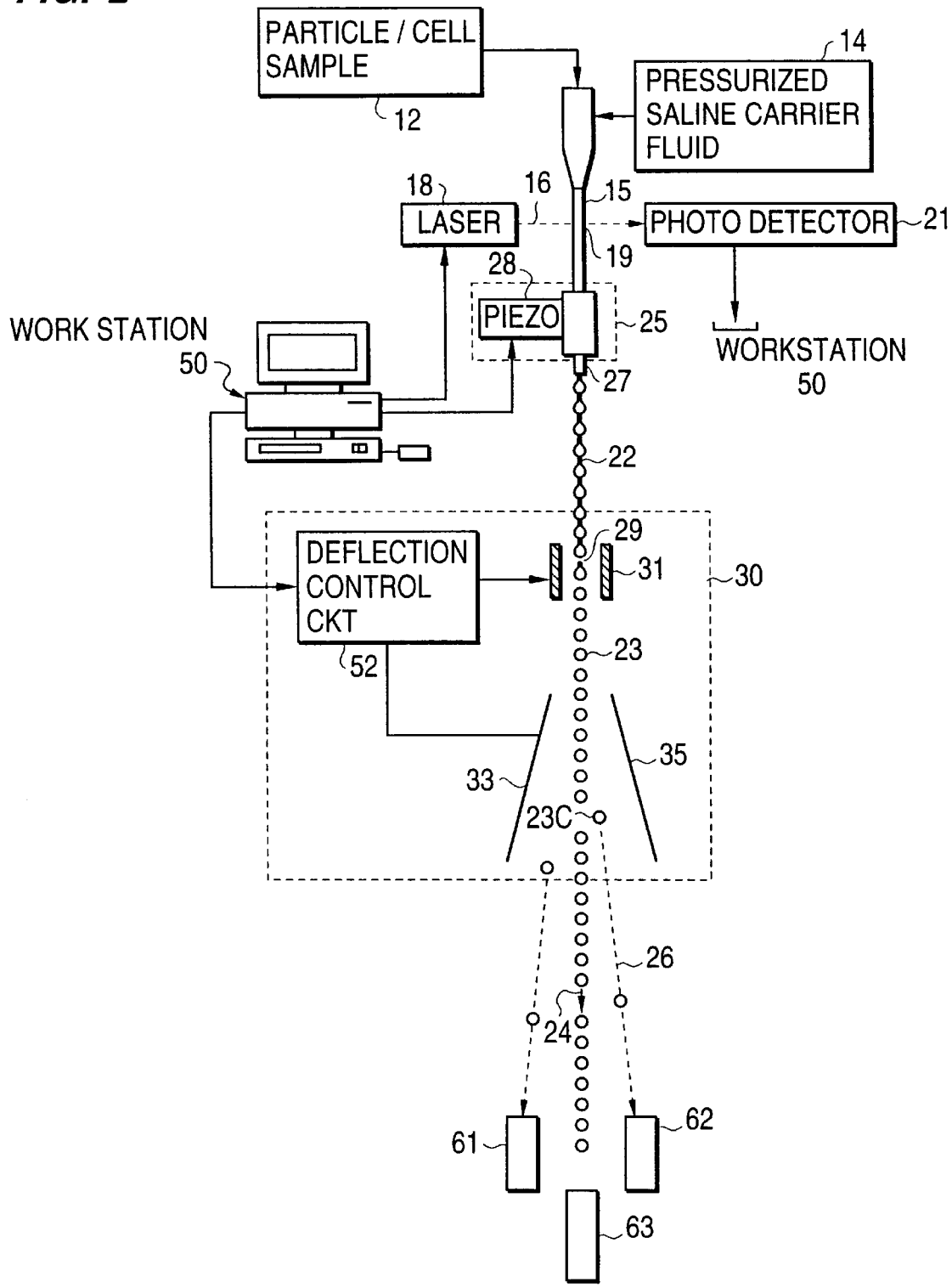
FIG. 2 diagrammatically illustrates the general instrumentation architecture of a flow cytometer system employing multiple reclaimable collection stores in accordance with the present invention.

FIG. 2 diagrammatically illustrates the instrumentation architecture of a flow cytometer system employing multiple reclaimable collection stores in accordance with the present invention. As shown therein the system comprises essentially the same components as shown in FIG. 1, described above, but with droplets being sortable to any of a plurality of particle reclamation containers 61 and 62 arranged on opposite sides of the main droplet travel path 24, or being unsorted directly to a waste or abort container 63. By reclamation container is meant a sorted droplet collection container or store, from which a quantity of extremely pure sorted droplets may be reclaimed for further use (such as reinjection back into the patient, as in the case of chemotherapy treatment, described above), or from which a quantity of less than extremely pure, but having a considerably higher density of desired particles/cells than that of the original container 12, may be retrieved for reprocessing through the cytometer sorting mechanism of the invention.

In addition, as will be described in detail below, in association with the use of a plurality of particle reclamation containers, the sort control routine executed by the system workstation 50 is operative to sort a respective fluid droplet based upon the contents of a plurality of contiguous droplet precursor regions within that portion of the fluid stream from which the droplet of interest will be formed, and also in adjacent portions of the fluid stream from which droplets on either side of the droplet of interest will be formed.

More particularly, as shown diagrammatically in FIG. 3, by droplet precursor region is meant one of a plurality of sequentially contiguous segments or regions 22-i within the carrier fluid 22, including its passage through the channel 15, that will eventually he contained within a respective droplet 23 that has broken off from the continuous fluid stream. The term 'precursor' is employed to reflect the fact that within the fluid stream 22 at a location upstream of the droplet separation location 29, including within that portion of the carrier fluid intersected by the laser output beam 16 at location 19, the fluid stream 22 may considered to be comprised of a sequence of contiguous regions that will 'eventually become, but are not yet formed into' an actual droplet—which breaks off from the uninterrupted fluid stream at droplet separation location 29.

The resolution to which the fluid within a respective droplet 23 may be subdivided into a plurality N of such droplet precursor regions may be established in accordance with the frequency of the clock signal, by which the sort delay or fluid travel time between laser beam intersection location 19 and droplet formation location 29 is measured, such as that used to clock a sort delay counter, as described above. As a non-limiting example, FIG. 4 shows a set of N=4 successively contiguous droplet precursor regions 22-1, 22--2, 22-3 and 22-4 within the fluid stream 22, that will eventually be formed into a respective droplet 23. Namely, the total volume of fluid and particles within the sequence of fluid regions 22-1 . . . 22-4 will occupy the same volume as the droplet 23 containing that amount of fluid and particles breaking off from the fluid stream at the droplet formation location. It should be observed that the number of such regions per droplet is not limited to this or any other number, but may vary in accordance with system parameters and user requirements.

Figure 5A:
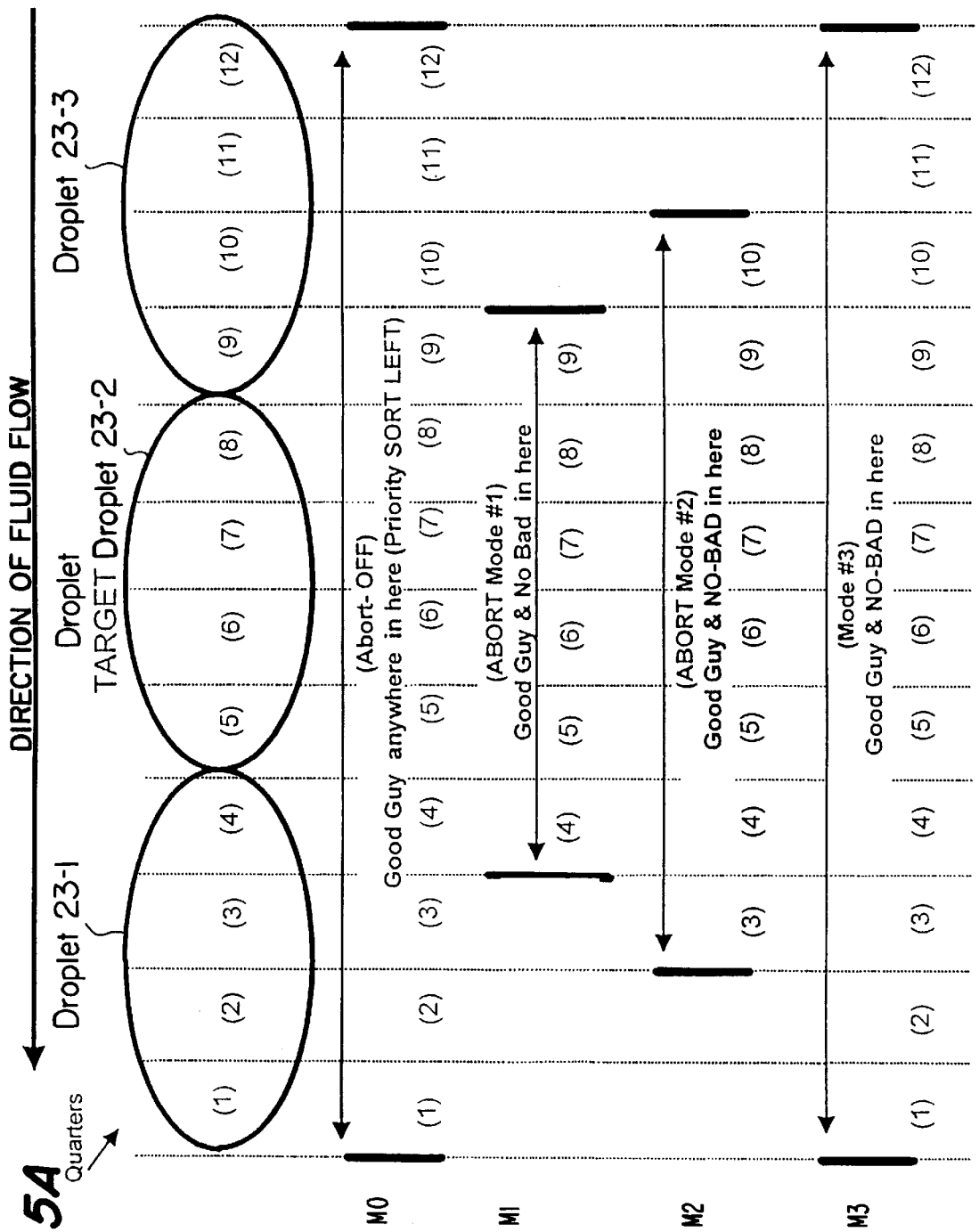
FIG. 5 diagrammatically illustrates the manner in which various modes of the sort control routine of the present invention controllably sort a respective target droplet based upon the contents of a plurality of contiguous droplet precursor regions for the target droplet and droplet precursor regions for droplets on either side of the target droplet.
Figure 5B:
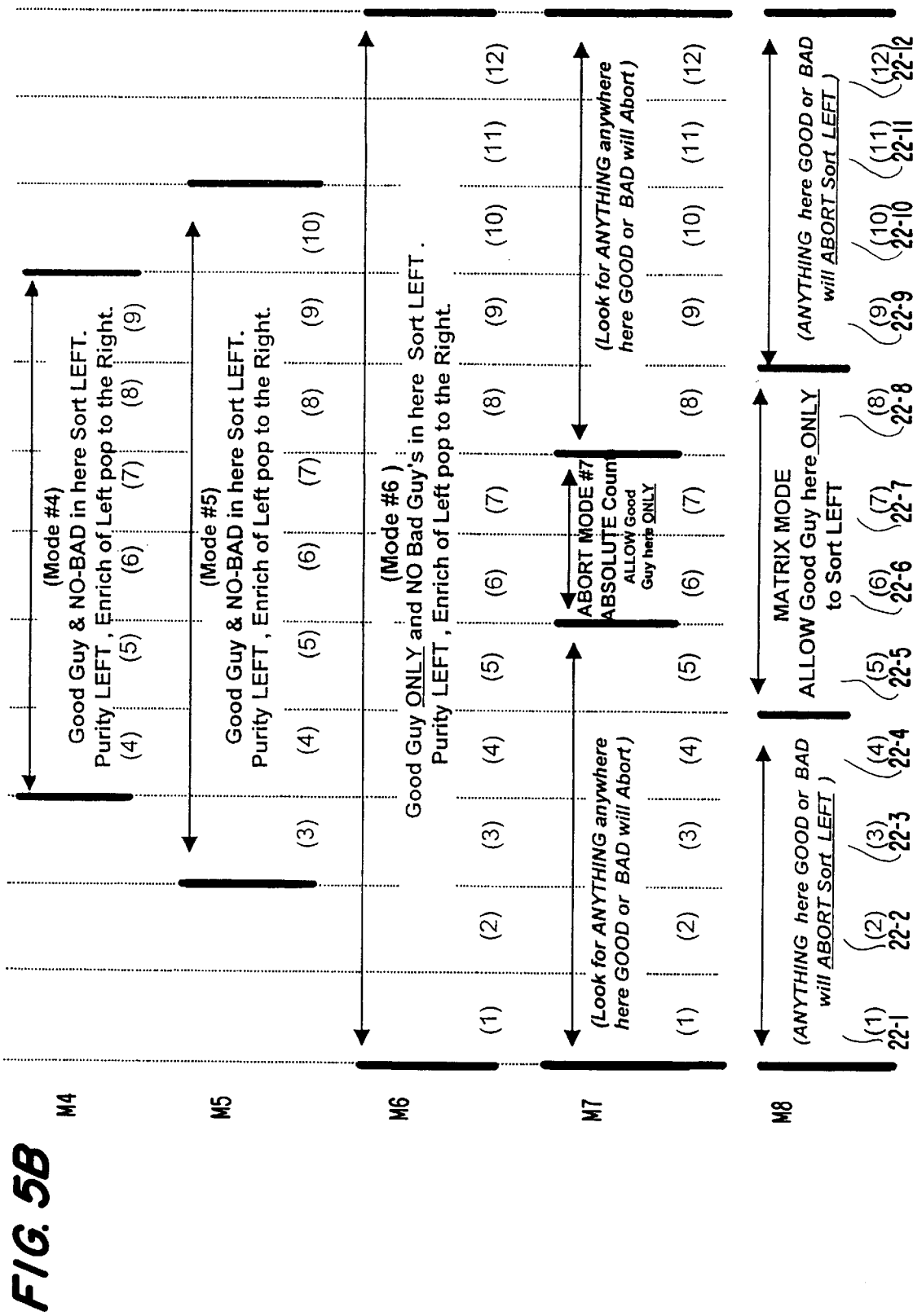

The manner in which the sort control routine of the present invention controllably sorts a respective fluid droplet based upon the contents of a plurality of contiguous droplet precursor regions for that droplet and droplet precursor regions on either side of the droplet of interest is diagrammatically shown in FIG. 5. For the present non-limiting example of a resolution of four droplet precursor regions per droplet, that portion of the continuous fluid flow stream 22 that will eventually become a 'target' droplet 23-2 of interest (i.e., the droplet to be sorted into one of the plurality of reclamation containers or to be aborted), comprises a center set of droplet precursor regions 22-5, 22-15, 22-7 and 22-8 within a sequence of twelve droplet precursor regions 22-1 . . . 22-12. Within the various mode listings the regions are denoted parenthetically as regions (1)–(12). This sequence of twelve droplet precursor regions defines what will be the contents of three immediately successive droplets, illustrated as a sequence of generally ellipse-shaped droplets 23-1, 23-2 and 23-2.

Shown directly beneath the sequence of twelve carrier fluid precursor regions 22-1 . . . 22-12 and their associated droplets 23-1, 23-2 and 23-3 are sorting criteria windows employed by respective sorting modes M0–M8, to be described individually below, to determine whether the center or second (target) droplet 23-2 in the sequence of three droplets 23-1, 23-2 and 23-3 is to be sorted or aborted and, if sorted, how it is to be sorted.

MODE M0 (MAXIMUM WIDTH SORT WINDOW—ABORT OFF)

This first sorting mode is intended to provide the highest yield of desired cells, but also allows particles other than the desired to be collected, so that the purity of the desired cells may be less than one hundred percent. In accordance with this first sorting mode, if a desired cell/particle of interest (labelled throughout FIG. 5 as a 'good guy') is found anywhere within a maximum sized sort window—one containing all twelve precursor regions 22-1 . . . 22-12, and regardless of the presence of an event/anomaly that might otherwise cause the droplet to be aborted (abort is turned off), a decision is made to sort the target droplet 22-2 to a selected one of the reclamation containers, such as the container 61 shown at the 'left' side of the droplet travel path 24. In FIG. 5, this sort decision is labelled as 'Priority SORT LEFT'. It should be noted that in this mode, in order to be sorted (left), the target droplet 23-2 need not actually contain a cell of interest. All that is required is that at least one of the twelve precursor regions 22-1 . . . 22-12 contain at least one desired cell.

MODE M1 (QUARTER DROPLET OVERLAP SORT WINDOW—ABORT ON)

This second sorting mode (and also the third and fourth sorting modes M2 and M3, respectively) is intended to sort either of two types of particles—one being sorted left to container 61 at the 'left' side of the droplet travel path 24, and the other being sorted right to container 62 at the 'right' side of the droplet travel path 24. In this sorting mode, the target droplet 23-2 will be sorted to that one of the reclamation containers that has been predetermined to collect the type of cell of interest only if the conditions set forth below are satisfied. Otherwise, the target droplet 23-2 will be aborted.

First, at least one of the two prescribed cell/particles of interest (each of which is a 'good guy') must be found anywhere within a six precursor region sort window containing all four regions 22-5 . . . 22-8 of the target droplet 23-2, immediately contiguous region 22-4 of adjacent downstream droplet 23-1, and immediately contiguous region 22-9 of upstream droplet 23-3.

Secondly, relative to a detected one of the two possible 'good guys', there must be no other type of cell or event (including the other type of good guy) within that six precursor region window. This latter requirement means that if the sort window contains both types of good guys it will be aborted.

As a non-limiting example, the fluid sample to be processed may contain two different types of blood cells that have been stained with red and green fluorescent dye antibodies, and which are to be collected in containers 61 and 62, respectively. In this case, if at least one green cell (a good guy) is detected within the six region window and no other (bad guy) type of cell or anomaly (such as but not limited to a red cell) is detected in that window, the target droplet 23-2 will be sorted right to the green cell container 62. Otherwise the target droplet will be aborted.

Conversely, if at least one red cell (also a good guy) is detected within the six region window and no other (bad guy) type of cell or anomaly (such as but not limited to a green cell) is detected in that window, the target droplet 23-2 will be sorted left to the red cell container 61. Otherwise, the target droplet 23-2 will be aborted.

As in the case of mode M0, it may be noted that in mode M1, the target droplet 23-2 need not actually contain a cell of interest to be sorted either right or left. All that is required is that at least one of the six precursor regions 22-4 . . . 22-9 contain at least one desired cell, and no bad cell.

MODE M2 (HALF DROPLET OVERLAP SORT WINDOW—ABORT ON)

As described above, this third sorting mode sorts either of two types of particles—one sorted left to container 61 at the 'left' side of the droplet travel path 24, and the other sorted right to container 62 at the 'right' side of the droplet travel path 24. Mode M2 is identical to mode M1 except that the sort window is expanded to cover a fifty percent overlap into the precursor regions of the adjacent droplets 23-1 and 23-3. Namely, in this third sorting mode, if either of two prescribed (good guy) cell/particle, of interest is found anywhere within an eight precursor region window containing all four regions 22-5 . . . 22-8 of the target droplet 23-2, the two immediately contiguous regions 22-3 and 22-4 of adjacent downstream droplet 23-1, and the two immediately contiguous region 22-9 and 22-10 of upstream droplet 23-3, and there is no other detected type of cell or event within the sort window, then a decision is made to sort the target droplet 23-2 to that one of the reclamation containers that has been predetermined to collect the type of cell of interest. Otherwise, the target droplet is aborted to waste container 63.

MODE M3 (FULL DROPLET OVERLAP SORT WINDOW—ABORT ON)

The fourth sorting mode M3 is identical to modes M1 and M2 except that the sort window is expanded to cover a full one hundred percent overlap into all of the precursor regions of the adjacent droplets 23-1 and 23-3. Namely, in this fourth sorting mode, if at least one of either of two prescribed (good guy) cell/particles of interest is found anywhere within a twelve precursor region window containing all four regions 22-1 . . . 22-4 of the first droplet 23-1, all four regions 22-5 . . . 22-8 of the target droplet 23-2, and all four regions 22-9 . . . 22-12 of the third droplet 23-3, and there is no other detected type of cell or event within the twelve region window, then a decision is made to sort the target droplet 23-2 to that one of the reclamation containers that has been predetermined to collect the type of cell of interest. Otherwise, the target droplet 23-2 is aborted.

MODE M4 (QUARTER DROPLET OVERLAP SORT WINDOW—ENRICHMENT SORT)

In the fifth sorting mode (and also the sixth and seventh sorting modes M5 and M6, respectively), the target droplet is never aborted. These modes are designed to sort only a given type of particle to a high purity container, such as into container 61 at the 'left' side of the droplet travel path 24, but otherwise sorting the target droplet to the other container, such as container 62 at the 'right' side of the droplet travel path 24, rather than aborting the target droplet. In other words, each of these modes is a dual sort mode for a given type of cell. Dual sort provides a high purity quantity of the desired cell in one reclamation container, and also provides a secondary container of 'good guy' cells, that may be reclaimed for further sorting.

This latter accumulation is due to the fact that in each of the fifth through seventh modes M4–M6, no detected or processed target cells are discarded or aborted. As a consequence, if an anomaly in the sort window prevents sorting to the high purity container what would otherwise be a target droplet containing at least one desired cell, rather than being aborted and losing what could be a significant number of desired cells, the target droplet will be sorted right to the enrichment container, the contents of which may be re-centrifuged and then processed again through the cytometer system of the invention.

In order to sort the target droplet to a high purity container, two requirements must be fulfilled. First, there must be at least one prescribed type of cell/particle ('good guy') within the sort window—a six precursor region window containing all four regions 22-5 . . . 22-8 of the target droplet 23-2, immediately contiguous region 22-4 of adjacent downstream droplet 23-1, and immediately contiguous region 22-9 of upstream droplet 23-3. Secondly, there must be no other type of cell or event within the six precursor region sort window. Only if both of these requirements are satisfied will the target droplet 23-2 be sorted to that one of the reclamation containers (e.g., sort left to container 61) that has been predetermined to collect the type of cell of interest.

For all other cases, the target droplet 23-2 will be sorted (right) to the other reclamation container 62, which effectively serves as an enrichment container. It may also be noted that in each of modes M4–M6, the target droplet 23-2 need not actually contain a cell of interest to be sorted left to the high purity container. All that is required is that at least one of the six precursor regions 22-4 . . . 22-9 contain a desired cell and no bad cell.

MODE M5 (HALF DROPLET OVERLAP SORT WINDOW—ENRICHMENT SORT)

Except for the size of the sorting window (expanded to eight precursor regions), the sixth sorting mode is identical to the fifth sorting mode, described above, and is designed to 'sort left' only a given type of particle to the high purity container 61, but otherwise sort the target droplet to the enrichment container 62. The eight precursor regions of the sorting window of mode M5 are all four regions 22-5 . . . 22-8 of the target droplet 23-2, the two immediately contiguous regions 22-3 and 22-4 of adjacent downstream droplet 23-1, and the two immediately contiguous regions 22-9 and 22-10 of upstream droplet 23-3.

MODE M6 (FULL DROPLET OVERLAP SORT WINDOW—ENRICHMENT SORT)

Mode M6 is identical to modes M4 and M5 except that the sort window is expanded to cover a full one hundred percent overlap into all of the precursor regions of the adjacent droplets 23-1 and 23-3.

It will be appreciated that the multiregion sorting window scheme of modes M4–M6 is particularly useful in reducing the time required to harvest a highly purified quantity of a particular type of cell. Not only are target droplets containing only desired cells sorted to a highly purified collect-ion store, but should an undesired cell be detected within a predefined proximity of a desired cell, rather than being simply aborted, the target droplet is sorted into an auxiliary 'enrichment' container, whose contents may then be reclaimed for resorting. As all target (desired cell-containing) droplets are sorted to one of a plurality of reclamation containers, no detected/processed cells are lost, as in conventional proximity based aborting decisions. As a consequence, through dual collection and resorting of the contents of the enrichment container the total harvest time can be significantly reduced.

As a non-limiting example, for the case of harvesting a one million (blood) cell population, with the mode M6 droplet overlap window for sorting target droplets containing only good cells at a data rate of 30,000 cells/sec. and a population density of one-half of one percent provides a potential yield rate of 150 possible cells per second. Because of the proximity of other types of cells, however, the sorted desired cell only population can be expected to be reduced by some percent (e.g., only fifty percent), resulting in an actual high purity yield rate of 75 cells per second. At this yield rate, the high purity container will accumulate a total quantity of 500K cells (half the desired cell population) in 500K/75 or 6,666 seconds=1.85 hours. For an enrichment container data rate of the remaining fifty percent of 150 target cells/sec., the corresponding yield rate is 75 cells/sec. During the time, at this auxiliary yield rate, the enrichment container will accumulate a total quantity of 500K desired cells in 500K/7500 or 66.66 seconds (1.1 hours), namely within the time (1.85 hours) required for the high purity container to accumulate 500K cells.

MODES M7 AND M8

Modes M7 and M8 are intended to provide a very high purity of desired cells by the use of relatively narrow inclusion windows. Each of these two modes employs a first, relatively narrow sorting inclusion window for desired cells only, that is bounded by a relatively wide exclusion window, in which the presence of any particles/cells will abort the target droplet.

MODE M7 (ABSOLUTE COUNT—ABORT ON)

Mode M7 is intended to provide a very high purity of desired cells. For this purpose, it employs a first, relatively narrow sorting inclusion window for desired cells only, that is bounded by a relatively wide exclusion window in which the presence of any particles/cells will abort the target droplet. More particularly, in this eighth sorting mode, in order to keep or sort the target droplet 23-2 to a reclamation container, at least one desired cell/particle of interest ('good guy') and no other types of particles or events must be found within a relatively narrow sorting inclusion window that consists of the middle two precursor regions 22-6 and 22-7 for the target droplet 23-2. Secondly, the remaining precursor regions 22-1 . . . 22-5 and 22-8 . . . 22-12 must be empty. Otherwise the target droplet is aborted.

MODE M8 (MATRIX MODE—ABORT ON)

Mode M8 is substantially the same as mode M7, except that the sorting inclusion window encompasses all of the precursor regions associated with the target droplet, and the exclusion window contains all of the precursor regions for the two adjacent droplets. Namely, in this ninth sorting mode, in order to keep or sort the target droplet 23-2 to a reclamation container, at least one desired cell/particle of interest ('good guy') and no other types of particles or events must be found within a sorting inclusion window that consists of all of the precursor regions 22-5 . . . 22-8 for the target droplet 23-2. Secondly, the precursor regions 22-1 . . . 22-4 for the adjacent downstream droplet 23-1 and the precursor regions 22-9 . . . 22-12 for the adjacent upstream droplet 23-3 must be empty. Otherwise the target droplet 23-2 is aborted.

As will be appreciated from the foregoing description, drawbacks of conventional flow cytometer sorting schemes are effectively remedied by the flow cytometer sorting mechanism of the invention, that is operative to controllably sort successively generated fluid droplets in accordance with the contents of a plurality of contiguous precursor regions of the carrier fluid which are contained within the target droplet of interest and precursor regions for droplets on either side of the target droplet. This multiregion sorting window scheme is particularly useful in reducing the time required to harvest a highly purified quantity of a particular type of cell, as not only are droplets containing only desired cells sorted to a highly purified collection store, but should an undesired cell be detected within a predefined proximity of a desired cell, rather than being simply aborted, the droplet is sorted into an auxiliary enrichment container, whose contents may then be reclaimed for resorting. Since all droplets are sorted to one of a plurality of reclamation containers, no detected/ processed cells are lost, as in conventional proximity based aborting decisions. As a consequence, through dual collection and resorting of the contents of the enrichment container the total harvest time can be significantly reduced.

While I have shown and described various embodiments in accordance with the present invention, it is to be understood that the same is not limited thereto but is susceptible to numerous changes and modifications as known to a person skilled in the art, and I therefore do not wish to be limited to the details shown and described herein, but intend to cover all such changes and modifications as are obvious to one of ordinary skill in the art.

What is claimed is:

1. A flow cytometer comprising a channel, through which a carrier fluid stream containing at least a prescribed component and potentially components other than said prescribed component flows, and which is intercepted by an optical energy beam illumination and detector subsystem, said subsystem being operative to generate output signals representative of contents of successive ones of contiguous droplet precursor regions as illuminated by said optical energy beam, said fluid stream containing a sequence of contiguous droplet precursor regions, that will eventually become, but are not yet formed into, droplets that are separated from said fluid stream by a downstream droplet generator to which said channel is coupled, and a droplet sorter through which said respective droplet pass, said droplet sorter being operative to sort said respective droplet to one of a plurality of droplet collection paths in response to an output signal generated by said subsystem being representative of the presence of said prescribed component in a selected number of droplet precursor regions within first, second and third pluralities of contiguous droplet precursor regions, and in accordance with contents of contiguous droplet precursor regions of said first, second and third pluralities of contiguous droplet precursor regions, other than said selected number of contiguous droplet precursor regions, said first, second and third pluralities of contiguous droplet precursor regions corresponding to respective first, second and third droplets that are separated from said fluid stream.

2. A flow cytometer according to claim 1, wherein said plurality of droplet collection paths include at least one container the contents of which are reclaimable.

3. A flow cytometer according to claim 1, wherein said selected number of contiguous droplet precursor regions of said fluid stream is less than all of the contiguous droplet precursor regions of said first plurality.

4. A flow cytometer according to claim 1, wherein said selected number of contiguous droplet precursor regions of said fluid stream includes all contiguous droplet precursor regions of said first plurality.

5. A flow cytometer according to claim 1, wherein said selected number of contiguous droplet precursor regions of said fluid stream includes contiguous droplet precursor regions of said first plurality, and contiguous droplet precursor regions of at least one of said second and third pluralities.

6. A flow cytometer according to claim 5, wherein said at least one of said second and third pluralities of contiguous droplet precursor regions includes both of said second and third pluralities of contiguous droplet precursor regions.

7. A flow cytometer according to claim 1, wherein said droplet sorter is operative to sort said respective droplet to said one of said plurality of droplet collection paths, in response to said subsystem detecting the presence of said prescribed component, but no other component, in said selected number of said contiguous droplet precursor regions of said first, second and third pluralities of contiguous droplet precursor regions.

8. A flow cytometer according to claim 1, wherein a respective droplet is obtained from fluid containing a plurality of blood cells, and wherein said prescribed component corresponds to a first type of blood cell.

9. A flow cytometer according to claim 1, wherein droplet sorter is operative to sort said respective droplet to a first droplet collection store in response to said selected number of contiguous droplet precursor regions containing only said prescribed component, but sorts said respective droplet to a second droplet collection store in response to said selected number of contiguous droplet precursor regions containing a component other than said prescribed component.

10. A flow cytomeater according to claim 1, wherein said droplet sorter is operative to sort said respective droplet to said one of a plurality of droplet collection paths in response to said subsystem detecting the presence of said prescribed component in any contiguous droplet precursor region of said first, second, and third pluralities of contiguous droplet precursor regions.

11. A method of sorting a respective droplet from a fluid stream containing a sequence of contiguous droplet precursor regions, that will eventually become, but are not yet formed into, droplets that separate from said fluid stream, said method comprising the steps of:

(a) subdividing said fluid stream into a first plurality of said contiguous droplet precursor regions that will become said respective droplet, and second and third pluralities of said contiguous droplet precursor regions on respective sides of said first plurality of said contiguous droplet precursor regions that will be formed into first and second droplets upstream and downstream of said respective droplet;

(b) examining a first number and a second number of contiguous droplet precursor regions with said first, second and third pluralities of contiguous droplet precursor regions of said fluid stream; and (c) sorting said respective droplet to a first droplet collection store, in response to said first number of contiguous droplet precursor regions within said first, second and third pluralities of contiguous droplet precursor regions of said fluid stream having a first chracteristic, and sorting said respective droplet to a second droplet collection store, in response to said second number of contiguous droplet precursor regions within said first, second and third pluralities of contiguous droplet precursor regions of said fluid stream having a second chracteristic.

12. A method according to claim 11, wherein step (c) comprises sorting said respective droplet to said first droplet collection store in response to said first number of contiguos droplet precursor regions also being exclusive of said second characteristic.

13. A method according to claim 12, wherein step (c) comprises sorting said respective droplet to a second droplet collection store in response to a second number of contiguous droplet precursor regions selected from among said first, second and third pluralities of contiguous droplet precursor regions having a second characteristic different from said first characteristic.

14. A method according to claim 11, wherein said first number of contiguous droplet precursor regions comprises contiguous droplet precursor regions of said respective droplet and said second and third pluralities of contiguous droplet precursor regions.

15. A method according to claim 11, wherein said first number of contiguous droplet precursor regions contains said first plurality of contiguous droplet precursor regions of said respective droplet and contiguous droplet precursor regions of said second and third pluralities of contiguous droplet precursor regions.

16. A method according to claim 11, wherein said first number of contiguous droplet precursor regions contains all of the contiguous droplet precursor regions of said respective droplet and less than all of the contiguous droplet precursor regions of said second and third pluralities of contiguous droplet precursor regions.

17. A method according to claim 11, wherein said first number of contiguous droplet precursor regions contains less than all contiguous droplet precursor regions of said first plurality of contiguous droplet precursor regions, and wherein said second number of contiguous droplet precursor regions contains contiguous droplet precursor regions of said second and third pluralities of contiguous droplet precursor regions.

18. A method according to claim 11, wherein step (c) comprises sorting said respective droplet to said first droplet collection store in response to said first number of contiguous droplet precursor regions containing only a first type of particle and in response to remaining contiguous droplet precursor regions of said first, second and third pluralities of contiguous droplet precursor regions containing no particle regardless of type, but otherwise sorting said respective droplet to said second droplet collection store.

19. A method according to claim 11, wherein step (c) comprises sorting said respective droplet to said first droplet collection store in response to said first number of contiguous droplet precursor regions containing only a first type of particle, but sorting said respective droplet to said second collection store in response to said first number of contiguous droplet precursor regions containing a particle other than said first type of particle.

20. A method according to claim 19, including the step of:
(d) sorting, in accordance with step (c), a respective droplet reclaimed from said second droplet collection store.

21. A method according to claim 19, wherein said respective droplet is obtained from fluid containing a plurality of blood cells, and wherein said first type of particle corresponds to a first type of blood cell, and said second type of particle corresponds to a particle other than said first type of blood cell.

22. A method according to claim 19, wherein said first number of contiguous droplet precursor regions comprises contiguous droplet precursor regions of said first plurality of contiguous droplet precursor regions and contiguous droplet precursor regions of said second and third pluralities of contiguous droplet precursor regions.

23. A method according to claim 19, wherein said first number of contiguous droplet precursor regions contains said first plurality of contiguous droplet precursor regions and continuous droplet precursor regions of said second and third pluralities of continuous droplet precursor regions.

24. A method according to claim 19, wherein said first number of contiguous droplet precursor regions contains all of the contiguous droplet precursor regions of said first plurality of contiguous droplet precursor regions and less than all of the contiguous droplet precursor regions of said second and third pluralities of contiguous drop of precursor regions.

25. A method of sorting a respective droplet from a fluid stream containing a sequence of contiguous droplet precursor regions, that will eventually become, but are not yet formed into, droplets that separate from said fluid stream, so as to accumulate a quantity of a prescribed component that may be present in said fluid stream, said method comprising the steps of:
(a) dividing said fluid stream into a first plurality of said contiguous droplet precursor regions of said fluid stream that will become said respective droplet, and second and third pluralities of said contiguous precursor droplet regions, on respective sides of said first plurality of said contiguous droplet precursor regions of said fluid stream, that will be formed into first and second droplets upstream and downstream of said respective droplet;
(b) examining first, second and third pluralities of said contiguous droplet precursor regions of said fluid stream for the presence of said prescribed component and components other than said prescribed component; and
(c) sorting said respective droplet to one of a plurality of droplet collection paths, in response to step (b) detecting the presence of said prescribed component in a selected number of droplet precursor regions within said first, second and third pluralities of contiguous droplet precursor regions, and in accordance with contents of contiguous droplet precursor regions of said first, second and third pluralities of contiguous droplet precursor regions, other than said selected number of contiguous droplet precursor regions.

26. A method according to claim 25, wherein said plurality of droplet collection paths include at least one container the contents of which are reclaimable.

27. A method according to claim 25, wherein said selected number of contiguous droplet precursor regions of said fluid stream is less than all of the contiguous droplet precursor regions of said first plurality.

28. A method according to claim 25, wherein said selected number of contiguous droplet precursor regions of said fluid stream includes all of the contiguous droplet precursor regions of said first plurality.

29. A method according to claim 25, wherein said selected number of contiguous droplet precursor regions of said fluid stream includes contiguous droplet precursor regions of said first plurality, and contiguous droplet precursor regions of at least one of said second and third pluralities of contiguous droplet precursor regions.

30. A method according to claim 29, wherein said at least one of said second and third pluralities of contiguous droplet precursor regions includes both of said second and third pluralities of contiguous droplet precursor regions.

31. A method according to claim 25, wherein step (c) comprises sorting said respective droplet to said one of said plurality of droplet collection paths, in response to step (b) detecting the presence of said prescribed component, but no other component, in said selected number of said contiguous droplet precursor regions of said fluid stream.

32. A method according to claim 25, wherein steps (a)–(c) are carried out in a flow cytometer.

33. A method according to claim 32, wherein said flow cytometer is configured to inject a sample containing at least said prescribed component and potentially components other than said prescribed component into a carrier fluid stream and to direct said carrier fluid stream along a channel that is intercepted by an optical energy beam illumination and detector subsystem, said subsystem being operative to generate output signals representative of contents of successive ones of said contiguous droplet precursor regions as droplets are formed, and a droplet sorter through which said respective droplet passes, and which is operative to sort said respective droplet to one of said plurality of droplet collection paths, in response to an output signal generated by said subsystem being representative of said presence of said prescribed component in said selected number of said contiguous droplet precursor regions within said first, second and third pluralities of contiguous droplet precursor regions, and in accordance with contents of contiguous droplet precursor regions of said first, second and third pluralities of contiguous droplet precursor regions, other than said selected number of contiguous droplet precursor regions.

34. A method according to claim 25, wherein a respective droplet is obtained from fluid containing a plurality of blood cells, and wherein said prescribed component corresponds to a first type of blood cell.

35. A method according to claim 25, wherein step (c) comprises sorting a respective droplet to a first droplet collection store in response to said selected number of contiguous droplet precursor regions containing only said prescribed component, but sorting said respective droplet to a second droplet collection store in response to said selected number of contiguous droplet precursor regions containing a component other than said prescribed component.

36. A method according to claim 35, including the step of:
(d) sorting, in accordance with step (c), a droplet reclaimed from said second droplet collection store.

37. A method according to claim 25, wherein step (c) comprises sorting said respective droplet to said one of a plurality of droplet collection paths in response to step (b) detecting the presence of said prescribed component in any contiguous droplet precursor region of said first, second and third pluralities of contiguous droplet precursor regions.

* * * * *